United States Patent [19]

Clever

[11] Patent Number: 5,710,329
[45] Date of Patent: Jan. 20, 1998

[54] ANTIFOULANT FOR ACRYLIC ACID PURIFICATION

[75] Inventor: Hester A. Clever, Sugar Land, Tex.

[73] Assignee: Nalco/Exxon Energy Chemical, L. P., Sugar Land, Tex.

[21] Appl. No.: 735,772

[22] Filed: Oct. 23, 1996

[51] Int. Cl.$^6$ .................................................. C07C 51/42
[52] U.S. Cl. .................................................. 562/600
[58] Field of Search .......................................... 562/600

[56] References Cited

U.S. PATENT DOCUMENTS

| | | | |
|---|---|---|---|
| 4,107,030 | 8/1978 | Slovinsky et al. | 208/48 AA |
| 4,902,824 | 2/1990 | Syrinek | 560/248 |

*Primary Examiner*—Gary Geist
*Assistant Examiner*—Rosalynd Keys
*Attorney, Agent, or Firm*—Robert A. Miller; Kelly L. Cummings; James J. Drake

[57] ABSTRACT

The invention comprises a method of dispersing foulants, residues, gums, precipitates, polymeric tars and other highly oxidized carbonaceous tars which can be formed in the process of manufacture and recovery of acrylic acid. The method comprises adding to the liquid or gaseous phases passing through, or stored in acrylic acid process equipment, an effective antifouling amount of a dispersant which is stable in the environment within an acrylic acid process and is compatible with the equipment used for the manufacture of acrylic acid.

7 Claims, No Drawings

ANTIFOULANT FOR ACRYLIC ACID PURIFICATION

BACKGROUND OF THE INVENTION

1. Field of the Invention

The invention relates to a method of dispersing foulants which are generated in an acrylic acid production unit.

2. Description of the Prior Art

Foulant formed in acrylic acid processes typically comprises poly(acrylic acid) and acrylic acid dimer, trimer, tetramer, etc. (poly(ester)). Poly(acrylic acid) is typically formed by the free-radical polymerization of acrylic acid. The dimer and the polyester are typically formed by the addition of acrylic acid across the carbon-carbon double bond. Fouling due to poly(acrylic acid) and addition products, if not cracked to the acrylic acid starting material, could be treated with a dispersant.

The use of dodecylbenzene sulfonic acid-containing products as dispersants in a vinyl acetate monomer production process is disclosed in U.S. Pat. No. 4,902,824, the disclosure of which is incorporated herein by reference. The '824 patent claims the use of benzene sulfonic acids in solvents as antifoulants for the vinyl acetate manufacturing process.

Similar fouling problems occur in acrylic acid production processes. Although many hydrocarbon production processes are superficially similar, it is often the case that compositions which are effective for a given application in one process are totally unsuitable in another. As exemplified in the instant application, the fact that benzene sulfonic acids effectively disperse foulant in the vinyl acetate manufacturing process, is not dispositive of whether benzene sulfonic acids would also disperse foulant in acrylic acid manufacturing processes. The nature of the monomers and of the fouling species in these areas are very different as described below.

The foulant in a vinyl acetate unit consists of poly(vinyl acetate), vinyl acetate oligomers, polymeric aldehydes, and oxidation products. Poly(vinyl acetate) and the vinyl acetate oligomers are formed by the free radical polymerization of vinyl acetate. Vinyl acetate dimers are formed by the addition of acetic acid across the carbon-carbon double bond of vinyl acetate. Aldol condensation of the aldehydes species result in oligomers and polymers. Other polymers related to the ethylene oxidation in the reactor section can also contribute to fouling.

The foulant in the acrylic acid process consists of poly (acrylic acid), acrylic acid dimer, and higher molecular weight addition products. Poly(acrylic acid) is formed by the radical polymerization of acrylic acid. The dimer of acrylic acid and the poly(ester), which are trimers, tetramers, pentamers, etc., are formed by the addition of acrylic acid across the carbon-carbon double bond.

The foulant species for each process are different. Poly (vinyl acetate) is soluble in its monomer, vinyl acetate. Poly(acrylic acid) is not soluble in its monomer, acrylic acid. The following tables, taken from the *Polymer Handbook*, list solvents and nonsolvents for poly(vinyl acetate), and poly (acrylic acid). Poly(vinyl acetate) is soluble in common organic solvents. Poly(acrylic acid) is soluble in polar solvents like water and DMF. The solvents for poly(vinyl acetate) have dipole moments in the range of 0–2 D. The solvents for poly(acrylic acid) have dipole moments in the range of 1.5–3.9 D.

| Solvents For Polymers of Vinyl Acetate and Acrylic Acid | |
|---|---|
| poly(vinyl acetate) solvents | poly(acrylic acid) solvents |
| 2,4-dimethyl-3-pentanol | alcohols |
| allyl alcohol | dilute alkali |
| benzene | dioxane/water 80:20 (isotactic) |
| acetone | DMF |
| acetic acid | formamide |
| benzyl alcohol | 1-methyl-2-pyridone |
| carbon tetrachloride/ethanol | |
| chlorobenzene | |
| chloroform | |
| dichloroethylene/ethanol 20:80. | |
| Dioxane | |
| ethanol/water | |
| glycol ether esters | |
| glycol ethers | |
| lower aliphatic esters | |
| methanol | |
| tetrahydrofurfuryl alcohol | |
| THF | |
| toluene | |

Polymer Handbook, 3rd ed., Branrup, J. and Immergut, E. H., eds., Wiley Interscience, New York, 1989.

| Nonsolvents For Polymers of Vinyl Acetate and Acrylic Acid | |
|---|---|
| poly(vinyl acetate) nonsolvents | poly(acrylic acid) nonsolvents |
| saturated hydrocarbons | hydrocarbons |
| mesitylene | esters |
| carbon tetrachloride | ketones |
| ethanol (anhydrous) | dioxane at higher temperatures |
| ethylene glycol | |
| cyclohexanol | |
| diethyl ether | |
| higher esters C > 5 | |
| carbon disulfide | |
| water | |
| dilute acids | |
| dilute alkalies | |

Polymer Handbook, 3rd ed., Branrup, J. and Immergut, E. H., eds., Wiley Interscience, New York, 1989.

Acrylic acid and poly(acrylic acid) are acidic species and exhibit the properties of an acidic species. They are polar, water soluble, and react with bases to form salts. Vinyl acetate is not an acidic species and does not exhibit these properties.

In summary, the foulant species in the vinyl acetate and acrylic acid processes exhibit vastly different physical characteristics. These differences include physical properties, solubilities, and reactivities. The interaction of dispersants with foulant material is dependent on properties like polarity (which correlates with dipole moment) and solubility.

Thus, the fact that dodecylbenzene sulfonic acid effectively disperses poly(vinyl acetate), a material that is soluble in vinyl acetate and common organic solvents, such as toluene, does not predict that it will effectively disperse poly(acrylic acid), a more polar material that is not soluble in its monomer, and is not soluble in any common organic solvent.

It would therefore be an advance in the art if one could simply add an effective amount of a dispersant to acrylic acid process equipment, so as to minimize or eliminate the possibility of foulant deposition which may inhibit the ability to achieve efficient use of the acrylic acid process equipment.

SUMMARY OF THE INVENTION

The invention comprises a method of dispersing foulants, residues, gums, precipitates, polymeric tars and other highly oxidized carbonaceous tars which can be formed in the process of manufacture and recovery of acrylic acid.

The method comprises adding to the liquid or gaseous phases passing through, or stored in acrylic acid process equipment, an effective antifouling amount of a dispersant which is stable in the environment within an acrylic acid process and is compatible with the equipment used for the manufacture of acrylic acid.

DESCRIPTION OF THE PREFERRED EMBODIMENTS

The dispersant which has been found that meets all of these requirements, i.e., a dispersant that effectively disperses foulant caused by polymeric tars, residues, highly oxidized carbonaceous tars and debris, and similar foulants as described above, while being compatible with the environment and chemicals used to manufacture acrylic acid, without causing difficulties in the manufacture of such monomer, are primarily those dispersants which are sulfonic acids. These sulfonic acids are exemplified by such materials as dodecylbenzene sulfonic acid, dioctyl sulfosuccinic acid, methane sulfonic acid and the like. These sulfonic acids may be used as is, or may be formulated in a compatible solvent, and may include, optionally, other dispersants, other surfactants, antifoaming agents, corrosion inhibitors, and similar ingredients.

The antifoulant formulation preferably used is one that contains dodecylbenzene sulfonic acid, and/or its salts, admixed and/or dissolved in an organic polar solvent, such a butyl cellosolve, an alkyl capped diether material available in commerce.

These antifoulants can contain from about 20 to about 100 weight percent sulfonic acid, preferably dodecylbenzene sulfonic acid, and/or its salts, admixed and/or dissolved in an organic polar solvent, such a butyl cellosolve, an alkyl capped diether material available in commerce.

These antifoulants can contain from about 20 to about 100 weight percent sulfonic acid, preferably dodecylbenzene sulfonic acid, and from about 0 to about 80 weight percent polar solvent, preferably butyl cellosolve.

In addition, the dodecylbenzene sulfonic acid may be present as its salts, particularly its quaternary ammonium or amine salts by neutralizing the sulfonic acid with various bases or with various amines, including polyamines and the like.

In addition to the dodecylbenzene sulfonic acid, other hydrocarbonaceous sulfonic acids may be used in the invention. These sulfonic acids may be alkyl or aryl sulfonic acids which may include, but are not limited to, such organic sulfonic acids as toluene sulfonic acid, methane sulfonic acid, dodecyl sulfosuccinic anhydride, dodecyl sulfosuccinic acid, and dioctyl sulfosuccinate. Representative of these sulfonic acids are those having the structure:

$R(SO_3)_nM$ wherein R is a hydrocarbonaceous group chosen from linear or branched alkyl groups, aromatic, cyclic, alkaryl, aralkyl, or alkenyl groups, and mixtures thereof; M is hydrogen, alkali metal, alkaline earth metal, ammonium cation, alkylamine cation, quaternary amine cation, and the like, or mixtures thereof; and n ranges from about 1 to about 6, preferably between about 1–4, and most preferably 1–2.

Also included in such effective sulfonic acids are structures which include alkyl aromatic sulfonic acids or alkyl naphthenic sulfonic acids.

The organic polar solvents to be used are solvents such as butyl cellosolve or any of the ethylene oxide based cellosolve capped ether solvents, and may also include such organic polar solvents as the diethyl ether of tetraethylene glycol, polyethylene and polypropylene oxide alkyl ethers, and generally may also include ketonic solvents such as acetone, or ester solvents such as ethyl acetate, or ether solvents such as diethyl ether or butyl cellosolve. In addition, other polar solvents that also function include certain organic acids such as acetic acid, or such other polar solvents as diacetone alcohol, linear alkyl and branched alkyl alcohols such as propanol, isopropanol, t-butanol, and the like. Admixtures of these polar solvents may also be used.

The alkyl sulfonic acids described above are preferred when used in process streams at concentrations ranging from about 10 ppm to about 20,000 ppm, based on the weight ratios of the additive formulation to the bottom stream to which the formula is added. However, hydrocarbonaceous sulfonic acids, or their formulations can function as antifoulants at treatment concentrations ranging from about 10–20,000 ppm, preferably between about 100–10,000 ppm and most preferably, between about 1000–7500 ppm treatment acid based on the process stream being treated.

Also, as can be seen, although the alkyl sulfonic acids can be used as amine salts, the activities of some amines, such as the heavy amine condensate salts are not as good as the activities of the free acids. Therefore, it is most preferred to use the sulfonic acids of the instant invention as the free acids.

| Dispersant | Dispersant Descriptions Description |
|---|---|
| A | poly(acrylate) |
| B | poly(acrylate) |
| C | phenolic polymer containing sulfonate groups |
| D | arylsulfonic acid/formaldehyde copolymer |
| E | a-olefin/maleic anhydride copolymer |
| F | aryl sulfonic acid |
| G | a-olefin/maleic anhydride copolymer |
| H | oxyalkylate |

The following examples are presented to describe preferred embodiments and utilities of the invention and are not meant to limit the invention unless otherwise stated in the claims appended hereto.

EXAMPLE 1

Eight dispersants were evaluated for compatibility in the process stream. Descriptions of these dispersants are given in the table. The aqueous dispersants, Dispersant A, Dispersant B, Dispersant C, and Dispersant D, precipitated when added to the process stream. Dispersant E also precipitated when added to this process stream. Dispersant F, Dispersant G, and Dispersant H were soluble in the stream and were used for further experiments.

EXAMPLE 2

The three soluble dispersants, Dispersant F, Dispersant G, and Dispersant H, were evaluated to determine their effectiveness at dispersing poly(acrylic acid), obtained from Aldrich Chemical Company, in the process stream. The polymer had a molecular weight of 2000. A slurry of poly(acrylic acid) in the process stream was prepared. This slurry (1 mL) was added to tubes containing 1000 ppm of the dispersants dissolved in the process stream. Poly(acrylic acid) settled to the bottom of the untreated tube. The poly(acrylic acid) dissolved in all the tubes containing the dispersants. An additional 0.1 g of solid poly(acrylic acid) was added to each tube. The polymer settled to the bottom of the untreated tube. The polymer began to dissolve in the tube containing Dispersant F. The polymer also began to dissolve in the tubes containing Dispersant G and Dispersant H, but not as quickly as that in the tube containing Dispersant F.

In order to differentiate among the dispersants, a higher concentration of dispersant was used. Using a higher concentration magnified the effectiveness of each dispersant. Dispersant F, Dispersant G, and Dispersant H (0.5 mL) were dissolved in 8 mL of the process stream. The solution of Dispersant G in the process stream was turbid, indicating an insoluble component at this concentration. Poly(acrylic acid) with a molecular weight of 2000, obtained from the Aldrich Chemical Company, (0.5 g) was added to each tube. All tubes were shaken. The tube containing Dispersant F had significantly less polymer settle to the bottom of the tube. Dispersant F appeared to increase the solubility of the poly(acrylic acid) in the process stream. There was no noticeable difference in the samples containing Dispersant G, Dispersant H, and no dispersant.

EXAMPLE 3

The dispersants were also tested using the foulant from an acrylic acid unit. The foulant was suspended in the process stream. This suspension (1 mL) was added to tubes containing dispersants in the process stream. Dispersant concentration was 1000 ppm. All foulant in tubes containing the dispersants settled at a slower rate than the foulant in the untreated tube. Some foulant remained suspended in all tubes, including the untreated tube, after 20 minutes. The experiment was repeated using 10,000 ppm dispersant with the same results.

The experiment was repeated using a five per cent dispersant. Initially, all of the tubes looked the same. After 12 hours, the tube containing Dispersant F was darker than at time zero. The undispersed poly(acrylic acid) foulant had a swollen appearance. No significant changes occurred in the tubes containing Dispersant G and Dispersant H. Dispersant F appeared to increase the solubility of the foulant in the process stream.

Changes may be made in the composition, operation and arrangement of the method of the present invention described herein without departing from the concept and scope of the invention as defined in the following claims:

I claim:

1. A method of dispersing tars, gums, and foulants in acrylic acid monomer process equipment which comprises adding to the liquid or gaseous phases contained therein an effective antifouling amount of an antifoulant, said antifoulant having the structure:

$$R(SO_3)_nM$$

wherein R is a hydrocarbonaceous group having from 1–34 carbon atoms chosen from linear or branched alkyl groups, aromatic, cyclic, alkaryl, aralkyl, or alkenyl groups, alkyl diphenyl ether groups, dialkyl naphthalene groups, or mixtures thereof; M is chosen from the group consisting of hydrogen, alkali metal, alkaline earth metal, ammonium cation, alkyl ammonium cation, or mixtures thereof; and n ranges from 1 to about 6.

2. The method of claim 1 wherein the antifoulant is chosen from the group consisting of dodecylbenzene sulfonic acid, methyl sulfonic acid, toluene sulfonic acid, alkyl diphenyl ether disulfonic acid, dialkyl naphthalene sulfonic acid, dioctyl sulfosuccinic acid, and mixtures thereof.

3. The method of claim 1 wherein the antifoulant is admixed with an organic polar solvent chosen from ketones, ethers, esters, alcohols, organic acids or mixtures thereof.

4. The method of claim 1 wherein the effective amount of antifoulant ranges between about 10–20,000 ppm antifoulant, based on the process stream being treated.

5. The method of claim 4 wherein the effective amount of antifoulant ranges between about 100–10,000 parts per million.

6. The method claim 5 wherein the effective amount ranges from about 1000–7500 parts per million antifoulant.

7. The method of claim 1 wherein the antifoulant is admixed with an organic polar solvent chosen from the group consisting of acetic acid, acetone, butyl cellosolve, ethyl acetate, diacetone alcohol, and mixtures thereof.

* * * * *